United States Patent [19]

Smets et al.

[11] Patent Number: 4,751,218

[45] Date of Patent: Jun. 14, 1988

[54] ACYLGLYCAN EXTRACTS OF KLEBSIELLA

[75] Inventors: Pierre Smets, Paris; René Zalisz, Menucourt, both of France

[73] Assignee: Roussel Uclaf, Paris, France

[21] Appl. No.: 804,687

[22] Filed: Dec. 4, 1985

[30] Foreign Application Priority Data

Dec. 6, 1984 [FR] France ............................. 84 18627

[51] Int. Cl.$^4$ ..................... A61K 31/70; A61K 37/10
[52] U.S. Cl. .......................................... 514/25; 514/8;
514/885; 536/4.1; 536/124
[58] Field of Search ................ 424/92, 195.1; 514/2,
514/8, 23, 25; 514/885; 536/4.1, 124

[56] References Cited

U.S. PATENT DOCUMENTS

| | | | |
|---|---|---|---|
| 3,929,994 | 12/1975 | Hirsch et al. | 514/8 |
| 4,356,171 | 10/1982 | Zalisz et al. | 424/92 |
| 4,501,693 | 2/1985 | L'Hinterland | 435/68 |

FOREIGN PATENT DOCUMENTS

| | | | |
|---|---|---|---|
| 0049182 | 4/1982 | European Pat. Off. | |
| 0089266 | 9/1983 | European Pat. Off. | 435/68 |
| 2043475 | 2/1971 | France . | |
| 2490496 | 3/1982 | France | 424/92 |

OTHER PUBLICATIONS

Biol. Abst. 76:26580, 1976.
Chem. Abst. 181:222,711a, 1984.
Chem. Abst. 72:29818v, 1970.

*Primary Examiner*—John Rollins
*Attorney, Agent, or Firm*—Bierman and Muserlian

[57] ABSTRACT

An acylglycan extract of Klebsiella consisting essentially of about 80% of neutral oses, about 20% of lipids and less than 2% of proteins and having a molecular weight of approximately 12,500 and a process for obtining them which have antiallergic and immunomodulating properties.

20 Claims, No Drawings

ACYLGLYCAN EXTRACTS OF KLEBSIELLA

STATE OF THE ART

Chemical Abstracts 72 (1970) 29818 v and Chemical Abstracts 101 (1984) 222712 b, Biological Abstracts 76 (1983) 26580 and BSM No. 7207 M describe various lipopolysaccharides. U.S. Pat. No. 4,501,693; U.S. Pat. No. 4,412,946; U.S. Pat. Nos. 3,855,197 and 3,929,994; U.S. Pat. No. 4,356,171 and French Pat. Nos. 2,462,477; No. 2,490,496; No. 2,043,475 describe glycoproteins or mixtures comprising glycoproteins and/or a process for their preparation but they are different from the products of the present invention.

OBJECTS OF THE INVENTION

It is an object of the invention to provide the novel acylglycan extracts of Klebsiella and a process for their preparation.

It is another object of the invention to provide novel antiallergic and immuno-modulating compositions and a novel method of inducing antiallergic and immunomodulating activity in warm-blooded animals.

These and other objects and advantages of the invention will become obvious from the following detailed description.

THE INVENTION

The novel products of the invention are an acylglycan extract of Klebsiella consisting essentially of about 80% neutral oses, about 20% of lipids and less than 2% of proteins and having a molecular weight of approximately 12,500.

Neutral oses means oses which do not have a basic or acid residue, particularly hexoses such as glucose, galactose, or mannose. They are determined by the Tillmans et al method (Biochem. Z., 1929, Vol. 215, p. 36) modified by Rimington (Biochem. J., 1931, Vol. 25, p. 1062). The proteins are determined by the Lowry method (J. Biol. Chem., 1951, Vol. 193, p. 265-273) and the lipids are determined by chromatography in vapor phase after methanolysis.

The molecular weight of the acylglcans of the present application has been estimated by filtration on hydrophilous and insoluble gel with a dextrane base such as Sephadex ® with a chromatography threshold of 50,000.

The preferred acylglycans are those for which the oses are present in the following approximate relative proportions, for 1 glucose: about 4 galactoses, about 1 mannose and about 1 heptose. This determination can for example, be carried out by chromatography in vapor phase. The more preferred acylglycans include a chain of galactoses linked at $\beta 1 \rightarrow 3$ with a molecular weight of about 9,000.

The acylglycans of the invention can be extracts of different species of Klebsiella. However, those derived from *Klebsiella pneumoniae* are preferred and more preferred are those of the strains with the numbers 52145 and I-163 at the Institut Pasteur of Collection Nationale de Culture de Microorganisms and at the National Culture Type Collection with the number 5, 055. This strain has been marketed for a long time and is freely available to the public, particularly from the Institut Pasteur at Paris with the reference 52 145. This strain has furthermore been filed by the applicant on the 25th June 1981 with the number I-163 at the Institut Pasteur (still called the Collection National de Cultures de Microorganisms).

In addition to oses and lipids, the acylglycans of invention are characterized by the presence of 2-keto-3-desoxy-octolosonic acid, glucosamines, phosphates, α and β-hydroxy myristic acids and of palmitic acid and the acylglycans of the invention appear in the form of a non-odorous, water-soluble white powder. Like all molecules of biological origin, they are hydrated or they hydrate easily and their infra-red spectrum is therefore not characteristic, the numerous peaks being confused. Their melting point is also not characteristic since carbonization takes place over a large range of temperatures.

The novel process of the invention for the preparation of said acylglycans comprises treating a water-soluble bacterial extract of Klebsiella containing 30% to 45% of proteins, 30% to 40% of neutral oses, a low proportion of uronic acids, 2% to 5% of osamines and having a molecular weight of about 350,000 with a detergent, heating the mixture to about 80° C., subjecting the mixture to chromatography on branched hydrophobic silica to recover the fraction corresponding to the elution peak revealed by spectrometry at 200 nm and disappearing at 280 nm, and appearing at 492 nm after coloring with sulfuric phenol. By a low proportion of uronic acids, there is intended less than 6% of uronic acids and preferably less than 4%.

The water-soluble bacterial extracts of Klebsiella used as starting material can preferably be obtained by culture of germs of the Klebsiella type, lysis of the germs, drying, delipidation by extraction of the lipids with solvents, ultra-filtration, treatment of the aqueous solution thus obtained with a quaternary ammonium salt, elimination of the precipitate, then either treatment in the cold of the supernatant with an alkanol of low molecular weight, separating then dissolving in water, dialysis and drying of the product obtained, putting back into solution, filtering on gel, then separation of the first eluted fraction and drying, or concentration of the supernatant by the use of at least one means of molecular selection, treatment in the cold of the concentrate with an alkanol and separation of the preciptate obtained.

Such preparations have already been described particularly in French Pat. No. 2,490,496 and in European Patent Application No. 0,049,182 published under the No. 29,070 E by Derwent Publications Farmdoc book No. 1,500 of Jun. 2, 1980 as well as in the French Patent Application No. 2,540,136.

Other starting water-soluble bacterial extracts of Klebsiella suitable for carrying out the process are, for example, obtained by putting the germ in culture, lysis of the germs by grinding, fractionated centrifuging to sediment the cellular waste under an acceleration of about 8,000 g, then the membranes under an acceleration of 20,000 to 40,000 g, separation of the crude extract by fractionated centrifuging in a saline solution and in water, treatment with a base or a hypobromite, elimination of the excess reagent and the insoluble residue, treatment with an aqueous solution of acetic acid at a temperature of 70° C. to 100° C., elimination of the insoluble fraction, delipidation by extraction of the lipids with solvents, treatment with lysozyme, separation of the fraction with a molecular weight of about 350,000 and drying. An example of such a preparation is described for example, in European Patent Application No. 0,089,266.

Products having detergent properties are well known and examples thereof are quaternary ammonium salts in particular quaternary ammonium halides such as tetraethylammonium iodide, N-hexadecyl-N,N-dimethylbenzene methanaminium chloride, N-hexadecyl-2-hydroxy-N,N,N-trimethyl-1-hexadecanaminium bromide, halides of N,N,N-trimethyl-1-hexadecanaminium or of cetylpyridinium. Other examples are alkaline sulfates or sulfonates of alkyl or alkylarylic ester type such as sodium dioctyl sulfosuccinate, sodium dodecylbenzene sulfonate, sodium dodecyl sulfate, sodium tetradecyl sulfate, lithium dodecylsulfate, polyethyleneglycols mono (nonylphenyl) ethers such as Triton N ®, polyethylene-glycols p-isooctyl phenyl-esthers such as Triton X ® or polymers of 4-(1,1,3,3-tetramethylbutyl)-phenol with formaldehyde and oxiame such as Triton ® A20. It is preferred to use an alkaline sulfate of the alkyl ester type such as sodium dodecyl sulfate.

The detergent is used in solution in a pharmaceutically acceptable solvent retaining in the detergent its detersive properties, preferably in solution in water. Depending upon the detergent power, it is used at a concentration of about 1% in the case of very detergent products such as sodium dodecyl sulfate, or more concentrated, for example 2% to 10% in the case of quaternary ammonium salts. The temperature of about 80° C. is maintained for a few minutes, preferably about 5 minutes.

The silica gel used for the chromatography is composed of silica on which hydrophobic groups are branched, preferably of fatty acids and the fatty acids can, for example, be fatty acids of 3 to 30 carbon atoms, preferably 3 to 20 carbon atoms. There is preferably used the gel $C_8$ sold under the name Aquapore ® RP300.

The identification of the interesting fraction of glucid nature and substantially lacking in proteins is carried out for example by spectrophotometry at 200 nm (detection of glucids and proteins), 280 nm (detection of proteins alone), 492 nm after coloring by sulfuric phenol (detection of sugars alone).

The elution is preferably carried out with graduated mixtures of acetonitrile and a 0.1% aqueous solution of trifluoroacetic acid with a pH of 1.8. The graduation is advantageously constituted successively with 20–80, then 50—50 mixtures of acetonitrile and the solution of trifluoroacetic acid. Under these conditions, the acylglycans sought correspond to the third peak revealed at 200 nm when a gel in $C_8$ is used and this peak disappears at 280 nm and appears at 492 nm after coloring with sulfuric phenol.

The isolation of the acylglycans is done in the usual manner for macromolecules mixed with small molecules, that is to say for example by ultrafiltration with membranes with a retention threshold of 5,000 for example, by dialysis or by chromatography on gel. The acylglycans can then be dried, for example, by lyophilization, evaporation or atomization.

The antiallergic and immuno-modulating compositions of the invention can comprised of an antiallergically and immuno-modulating effective amount of an acylglycan of the invention and an inert pharmaceutical carrier or excipient. The compositions may be in the form of tablets, dragees, gelules, granules, solutions, syrups, suppositories, lyophilized or non-lyophilized injectable preparations, ovules, creams, ointments, lotions, drops, collyria and aerosols.

Examples of suitable excipients are talc, gum arabic, lactose, starch, magnesium stearate, cocoa butter, aqueous or non-aqueous vehicles, fatty substances of animal or vegetable origin, paraffin derivatives and preservatives.

Due to their immuno-stimulating activity and especially stimulating immunity to cellular mediation, the acylglycans are useful for stimulating the secretion of Interleukine I and Colony Stimulating Factor as well as mitogenic activity. The acylglycans are also useful for the treatment or prevention of infectious illnesses caused by bacteria or viruses, in the treatment of parasitic diseases, of toxic infections, in the treatment of post hospital and post surgical infections and for allergies of all origins.

For the prevention use, the acylglycans may be used alone. They may also be used as adjuvant in vaccine.

The novel method of treating allergies and inducing immuno-modulating activity in warm-blooded animals, including humans, comprises administering to warm-blooded animals an anti-allergically and immuno-modulating effective amount of an acylglycan of the invention. The products may be administered topically, orally, rectally or parenterally and the usual effective daily dose is 0.025 to 0.15 mg/kg depending on the condition treated and the method of administration. For example, the product of Example 1 may be orally administered at a daily dose of 0.03 to 0.15 mg/kg for the treatment of chronic bronchitis.

In the following examples there are described several preferred embodiments to illustrate the invention. However it is to be understood that the invention is not intended to be limited to the specific embodiments.

EXAMPLE 1

7.83 ml of a 1% sodium dodecyl sulfate aqueous solution were added to 235 mg of a water-soluble bacterial extract of Klebsiella prepared as indicated below according to option b, and the mixture was heated for 5 minutes at 80° C. After cooling, chromatography in fractions of 0.5 ml was carried out on a column for high performance liquid chromatography (HPLC) of silica grafted with fatty acids in $C_8$ (Aquapor ® RP 300 of 4.6×25 cm) and elution with a graduated acetonitrile - 0.1% (pH 1.8) trifluoroacetic acid aqueous solution with a flow of 2 ml/mn was effected under the following conditions (cf. Table below):

| Time | Acetonitrile | Water |
| --- | --- | --- |
| 0 | 0 | 100 |
| 10 | 0 | 100 |
| 20 | 20 | 80 |
| 35 | 20 | 80 |
| 45 | 50 | 50 |
| 60 | 50 | 50 |
| 80 | 100 | 0 |

The fractions corresponding to the third peak revealed by spectrometry at 200 nm were isolated and the small molecules were eliminated by dialysis. The remainder was dried to obtain 67.85 mg of the expected acylglycans.

Analysis: % C: 42 % H: 7.8 % N 0.3. Proteins 0.8%, sugars 80%, lipids 24.5%.

Preparation of the water soluble bacterial starting extract of Klebsiella was as follows:

Step A: culture

A culture medium was prepared containing the following ingredients:

| | |
|---|---|
| meat extract | 690 g |
| sodium chloride | 690 g |
| casein peptone | 690 g |
| yeast autolysate | 690 g |
| bipotassium phosphate | 483 g |
| monopotassium phosphate | 207 g |
| glucose | 4104 g |
| soya papainic peptone | 2760 g |
| distilled water q.s. | 138 liters. |

The culture medium was prepared by successively mixing the meat extract, the sodium chloride, the casein peptone, the yeast autolysate, the bipotassium phosphate and the monopotassium phosphate in about 20 liters of distilled water and the pH was adjusted to about 7. The medium was sterilized at 120° C. for 40 minutes and the glucose and soya papainic peptone solutions were introduced into the culture medium at the moment of inoculation after having been sterilized previously.

The Klebsiella strain (Institute Pasteur No. I-163) was inoculated into 50 ml of culture medium and this solution serving as inoculum was introduced into the remainder of the culture broth. The total volume of the culture medium was adjusted to 138 liters by the addition of sterile distilled water. The culture medium was maintained at 37° C. and the pH was automatically adjusted to about 7 by the addition of an ammonia solution or by the addition of a hydrochloric acid solution. The growth of the germs was evaluated by a photometer.

STEP B: lysis

An aqueous solution of lysozyme hydrochloride, sterilized by filtration on membrane, was added to 138 liters of fully developed culture broth obtained in Step A to have a final concentration of 160 γ of lysozyme hydrochloride per ml of culture medium. The mixture stood for one hour at 56° C. in the presence of 0.25 g of Edta per liter of broth, 862.5 mg of sodium mercurothiolate and 80 g of polysorbate (marketed under the name of Tween 80), per liter of culture broth. Lysis was continued for about 10 days at 37° C. in sterile conditions and the lysate was recovered, homogenized by stirring, then lyophilized.

STEP C: treatment (a) By acetone:

The powder obtained in Step B was suspended in 138 liters of acetone and the mixture was vigorously stirred for about 3 hours. The suspension was then centrifuged and powder was collected which was dried.

(b) By methanol:

The powder obtained previously was suspended in 138 liters of methanol and the mixture was vigorously stirred for about 3 hours. The suspension obtained was then centrifuged and the separated powder was dried at ambient temperature under reduced pressure.

STEP D: Ultrafiltration

Six equal parts of powder obtained in Step C were dissolved in 6 lots of 10 liters of distilled water containing 1 g/l of merthiolate. The solution was maintained with stirring at +4° C. for 24 hours and was then centrifuged for about 2 hours at 20,000 g, then at 60,000 g. The solution was recovered and made up to 10 liters with filtered distilled water (on sterilizing membrane). The solution obtained was introduced into a diafiltration apparatus equipped with porous membranes for ultrafiltration, the retention threshold of which is 300,000 and the apparent diameter of the pores is 2A (membranes marketed by the AMICON company or by the ROMICON company under the name of XM 300). 50 volumes of distilled water were circulated in the apparatus, that is a volume of 500 liters. The diafiltered solution was recovered and then was centrifuged at 60,000 g and the solution obtained was lyophilized.

STEP E: Option a:

20 g of product obtained in Step D were dissolved in two liters of permuted water and about 1.6 liters of 3% cetyltrimethylammonium bromide in water were added slowly. The mixture was stirred for an hour, then centrifuged at 10,000 rpm for 15 minutes. The precipitate was eliminated and 3 liters of ethanol were added to the isolated supernatant at 95° C. over 15 minutes. After an hour of stirring, followed by centrifuging at 10,000 rpm for 15 minutes, the supernatant was eliminated and the precipitate was dissolved in 1 liter of water, then dialyzed for 48 hours in Visking ® tubes against permuted water at +4° C. At the end of this dialysis, the solution was lyophilized to obtain 6.2 g of glycoproteins, 1 g of which was dissolved in 19 ml of a 0.1M aqueous solution of ammonium carbonate. The solution was passed on a column of 2.5 cm diameter containing 1 liter of Ultragel ® ACA34 (eluent: 0.1M aqueous solution of ammonium carbonate). The fractions corresponding to the first elution peak (detection with U.V. at 280 nm) were combined and lyophilized to obtain 0.51 g of water-soluble bacterial extract of Klebsiella.

Option b:

1 kg of product obtained in Step D was dissolved in water at 10 g/1 liter and 0.8 volume of 3% aqueous solution of cetyltrimethylammonium bromide was added at the rate of about 1 liter/minute. The mixture was stirred moderately for 1 hour and the precipitate formed was eliminated by continuous centrifuging with a flow of about 5 liters/hour at 62,000 g. The supernatant was concentrated by ultrafiltration on hollow fibers with a retention threshold fixed at 5,000 (Hollow Fibers H10P5 marketed by AMINCO and ROMICON) in 2 cycles of treatment in proportions of 5/1. 6 volumes of 96% ethanol were added at the rate of 3 liters per minute and the mixture was stirred for 15 minutes. After decanting and separating, the precipitate was rinsed, dried at less than 40° C. in the presence of a dehydrating agent, homogenized by mechanical grinding to obtain 200 g of water-soluble bacterial extract of Klebsiella.

EXAMPLE 2

Tablets were prepared containing 1 mg of the product of Example 1 and sufficient excipient of lactose, starch, talc and magnesium stearate for a final tablet weight of 100 mg.

EXAMPLE 3

Aerosols were prepared to deliver doses containing 0.5 mg of the product of Example 1, 0.15 mg of emulsifier and 50 mg of propellant.

EXAMPLE 4

A cream was prepared containing 1 mg of the product of Example 1 and sufficient excipient of 2-octyldodecanol alcohol, cetostearylic alcohol, sodium cetostearyl sulfate, methyl and propyl parahydroxybenzoate and purified water for a total weight of 10 mg.

PHARMACOLOGICAL DATA (1) Test of delayed hypersensitivity response (DHS) to red corpuscle of sheep (RCS)

The test was carried out on batches of 10 female mice aged from 9 to 10 weeks weighing about 20 q. The treatment was carried out 3 hours before immunization with RCS by an intraperitoneal injection of 0.5 ml of 9°/.. NaCl containing the test product. The doses tested were 10, 100 and $1000 \times 10^{-6}$ g per Kg. The immunization was carried out 3 hours after treatment with intravenous injection of RCS. ($10^8$ RCS/mouse). The development of DHS was carried out 4 days later by intraplantal injection in the rear left paw of $40 \times 10^{-6}$ liter of a suspension of RCS.

The readings were determined 24 hours after the development by measuring the thickness of the rear left and right paws. The results were expressed as the difference between the thickness of the rear left and right paws of each mouse and the results are expressed in the following table:

|  | TREATMENT $10^{-6}$ g/kg | DIFFERENCE nm |
| --- | --- | --- |
| Control batch | 0 | 3.23 ± 0.76 |
| Batch treated | 10 | 4.74 ± 0.95 |
|  | 100 | 6.33 ± 0.93 |
|  | 1000 | 9.00 ± 1.80 |

Any increase in the difference between left and right paw in relation to the control batch means an increase in responses of delayed hypersensitivity. It is noted that for all the studied doses (10; 100; 1000 $10^{-6}$ g/kg), the acylglycans of the invention increase the DHS responses in a notable manner.

(2) Acute toxicity

The lethal doses 50 (LD 50) by intraperitoneal route in mice was determined by the BEHRENS and KARBER method and was about 20 mg/kg for the acylglycans of Example 1.

Various modifications of the products and method of the invention may be made without departing from the spirit or scope thereof and it should be understood that the invention is intended to be limited only as defined in the appended claims.

What we claim is:

1. An acylglycan extract of Klebsiella consisting essentially of about 80% of neutral oses, about 20% of lipids and less than 2% of proteins and having a molecular weight of approximately 12,500.

2. An acylglycan of claim 1 wherein the oses are present in the following approximate relative proportions: for 1 glucose: about 4 galactoses, about 1 mannose and about 1 heptose.

3. An acylglycan of claim 2 wherein they include a chain of galactoses linked at $\beta1 \rightarrow 3$ with a molecular weight of about 9,000.

4. An acylglycan of claim 1 wherein they include a chain of galactoses linked at $\beta1 \rightarrow 3$ with a molecular weight of about 9,000.

5. An acylglycan of claim 1 wherein the extract is from Klebsiella pneumoniae.

6. An anti-allergic composition comprising an anti-allergically effective amount of an acylglycan of claim 1 and an inert pharmaceutical carrier.

7. A composition of claim 6 wherein the oses are present in the following approximate relative proportions: for 1 glucose: about 4 galactoses, about 1 mannose and about 1 heptose.

8. A composition of claim 6 wherein the acylglycan includes a chain of galactoses linked at $\beta1 \rightarrow 3$ with a molecular weight of about 9,000.

9. A composition of claim 6 wherein the microbial extract is from *Klebsiella pneumoniae*.

10. A process for the preparation of an acylglycan of claim 1 comprising adding to a water-soluble bacterial extract of Klebsiella containing 30% to 45% of proteins, 30% to 40% of neutral oses, a low proportion of uronic acids, 2% to 5% of osamines and having a molecular weight of about 350,000 a detergent, heating the mixture to about 80° C., subjecting the mixture to chromatography on branched hydrophobic silica to recover the fraction corresponding to the elution peak revealed by spectrometry at 200 nm and disappearing at 280 nm and appearing at 492 nm after coloring with sulfuric phenol.

11. The process of claim 10 wherein the water-soluble bacterial extract was obtained by culturing germs of the Klebsiella type, lysis of the germs, drying, delipidation by extraction with solvents of lipids, ultra-filtration, adding to the aqueous solution thus obtained a quaternary ammonium salt, elimination of the precipitate, then either adding in the cold of the supernatant an alkanol of low molecular weight, isolation, then dissolving in water, dialysis and drying of the product obtained, putting it back into solution, filtration on gel then isolation of the first eluted fraction and drying, or concentration of the supernatant by using at least one molecule selection means, treatment in the cold of the concentrate with an alkanol and isolation of the precipitate obtained.

12. An acylgylcan extract produced by the process of claim 10.

13. A method of treating or prevent allergic reactions in warm-blooded animals comprising administering to warm-blooded animals an anti-allergically effective amount of an acylglycan of claim 1.

14. A method of claim 13 wherein the oses are present in the following approximate relative proportions: for 1 glucose: about 4 galactoses, about 1 mannose and about 1 heptose.

15. A method of claim 13 wherein the acylglycan includes a chain of galactoses linked at $\beta1 \rightarrow 3$ with a molecular weight of about 9,000.

16. A method of claim 13 wherein the microbial extract is from *Klebsiella pnenmoniae*.

17. A method of inducing immuno-modulating activity in warm-blooded animals comprising administering to warm-blooded animals an immuno-modulating effective amount of an acylglycan of claim 1.

18. A method of claim 17 wherein the oses are present in the following approximate relative proportions: for 1 glucose: about 4 galactoses, about 1 mannose and about 1 heptose.

19. A method of claim 17 wherein the acyglycan includes a chain of galactoses linked at $\beta1 \rightarrow 3$ with a molecular weight of about 9,000.

20. A method of claim 17 wherein the microbial extract is from *Klebsiella pneumoniae*.

* * * * *